United States Patent [19]

Shono

[11] 4,159,304
[45] Jun. 26, 1979

[54] PORTABLE GAS DETECTION TUBE HOLDER

[75] Inventor: Kyoichi Shono, Machida, Japan

[73] Assignee: Gastec Company Limited, Tokyo, Japan

[21] Appl. No.: 888,296

[22] Filed: Mar. 20, 1978

[30] Foreign Application Priority Data

Dec. 13, 1977 [JP] Japan .............................. 52-166533[U]

[51] Int. Cl.² .............................................. G01N 1/22
[52] U.S. Cl. ....................................... 422/104; 422/59; 422/86
[58] Field of Search ...................... 23/292, 254 R, 259; 73/28, 421.5 R; 422/59, 86, 102, 103, 104

[56] References Cited

U.S. PATENT DOCUMENTS

| 3,223,487 | 12/1965 | Grosskopf | 23/254 R |
| 3,239,311 | 3/1966 | Luehrmann et al. | 23/292 |
| 3,250,395 | 5/1966 | Blume | 23/292 X |
| 3,388,975 | 6/1966 | Wallace | 23/254 R |
| 3,482,944 | 12/1969 | Plantz | 23/254 R |

Primary Examiner—Arnold Turk
Attorney, Agent, or Firm—Koda and Androlia

[57] ABSTRACT

Portable gas detection tube holder which comprises a hollow cylindrical main body, a flanged tubular gas detection tube mounting member received in said main body, a hinge-type clip rotatably attached to the side of said main body, a hollow suction pipe connection member connected at one end to one end of said main body and adapted to be connected at the other end to the suction pipe of a small portable metering pump worn by a worker, said suction pipe connection member being in communication with the main body and said gas detection tube mounting member, and a tubular transparent gas detection tube protection member received at one end in the other end of said main body and having a bored end member fitted on the other end of said protection member.

9 Claims, 6 Drawing Figures

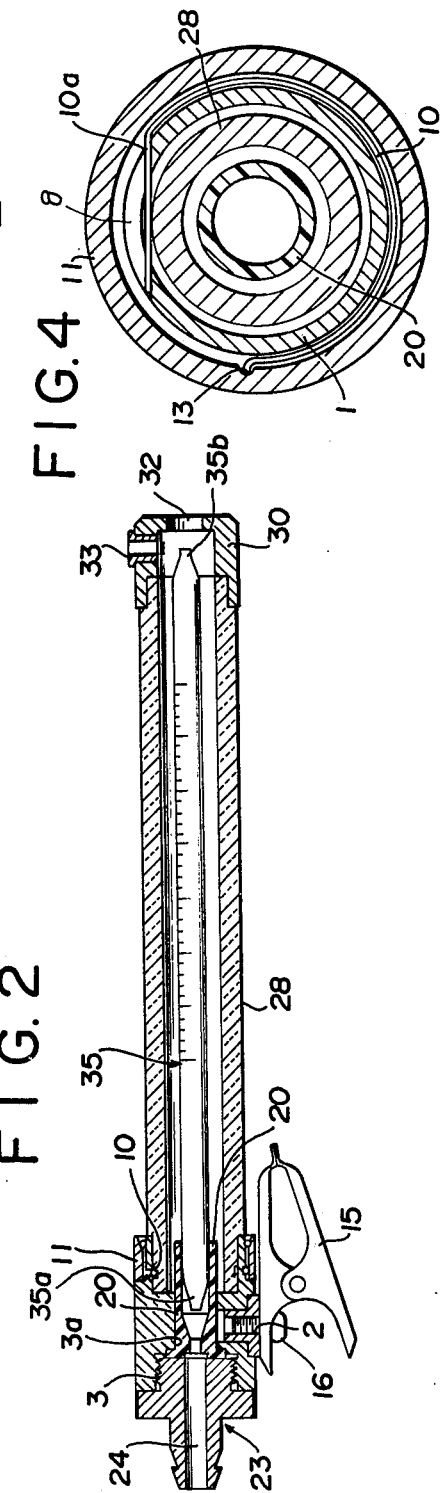
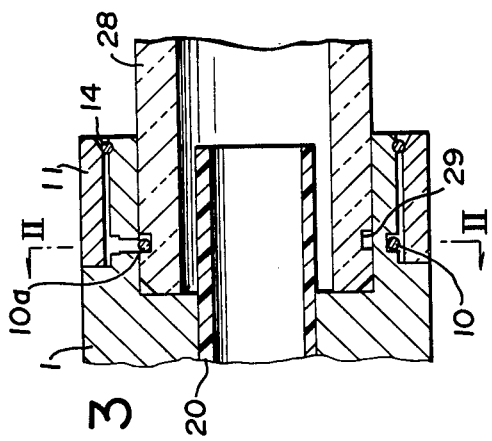
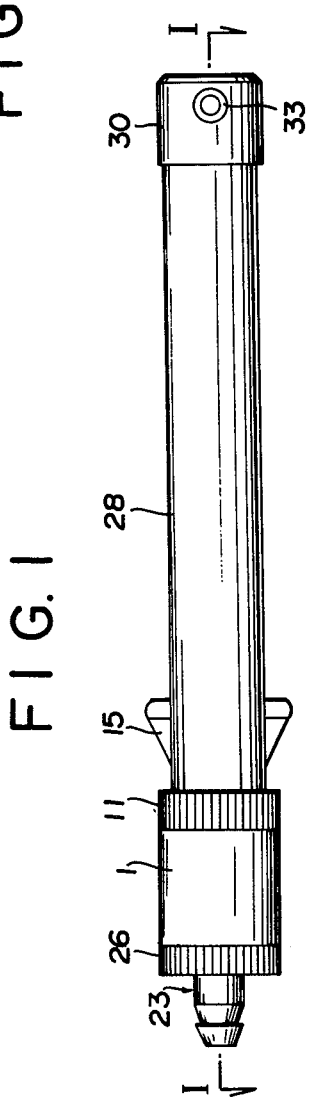

PORTABLE GAS DETECTION TUBE HOLDER

BACKGROUND OF THE INVENTION

This invention relates to a novel and improved portable gas detection tube holder and more particularly, to the joint which connects between the main body and the gas detection tube protection member of the holder.

When an operation is carried out in a workshop and other areas where gases harmful to human bodies tend to generate and/or oxygen tends to run out, it is necessary to provide means by which the worker can perform his assigned operation while maintaining his gas breathing-in level within a permissible gas inhalation range and readily become aware of sudden generation of toxic gases at high levels when such gases generated. Thus, it is the present practice that when an operation is to be performed at the areas where toxic gases tend to generate, each worker performs the operation while carrying a gas detection device with him. For example, the worker wears a small-type pump which sucks and discharges air through its suction and discharge pipes, respectively, at a metered amount per unit time and an associated gas detection tube connected to the suction pipe on his body. The gas detection tube contains an amount of gas reactive reagent therein and the reagent is of the type which changes its color in proportion to the amount of gases which pass through the reagent. When the toxic gases have generated at the working area, the pump is operated to pump air which entrains the gases to and through the reagent contained in the gas detection tube which then discolors over a portion or length in proportion to the amount of the gases which has passed through the reagent per unit time to thereby determine the amount of gases which the worker inhales per unit time.

However, the prior art gas detection tube has been generally carried about by the worker by being placed in a pocket of his jacket or other clothing and easily subjected to damage because the worker frequently forgets the presence of the gas detection tube in his jacket pocket while he is working resulting in that the pocket having the detection tube therein strikes against a hard article.

SUMMARY OF THE INVENTION

Therefore, the purpose of the present invention is to provide a novel and improved holder for a portable gas detection tube which can effectively and positively attach the gas detection tube to a portion of a worker's jacket or other clothing such as an upper jacket pocket. The holder effectively safeguards the portable gas detection tube against possible damage and is easy in handling and simple in construction.

In order to attain the purpose, according to the present invention, there has been provided a portable gas detection tube holder which essentially comprises a hollow cylindrical main body, a tubular suction pipe connection member connected at one end to one end of said main body and adapted to be connected at the other to the suction pipe of a portable metering pump worn by a worker, a hinge-type clip rotatably attached to the side of said main body for detachably securing the main body to said worker's upper jacket, a tubular detection tube mounting member received in said main body extending into the other end of said main body for receiving one end of a gas detection tube, said detection tube mounting member being in communication with said main body and suction pipe connection member and tubular gas detection tube protection member detachably and snuggly received at one end between said other end of the main body and gas detection tube mounting member for receiving a gas detection tube therein and having an end member fitted at the other end thereof and provided with a gas detection tube breaking means.

The above and other objects and attendant advantages of the present invention will be more readily apparent to those skilled in the art from a reading of the following detailed description in connection with the accompanying drawings which show one preferred embodiment of the invention for illustration purpose only, but not for limiting the scope of the same in any way.

BRIEF DESCRIPTION OF THE DRAWINGS

The accompanying drawings show one preferred embodiment of holder for a portable gas detection tube constructed in accordance with the present invention and in which:

FIG. 1 is a side view of a portable gas detection tube on which the holder of the invention is employed;

FIG. 2 is a longitudinally sectional view taken substantially along the line I—I and as seen in the arrow direction of FIG. 1;

FIG. 3 is a fragmentary sectional view on an enlarged scale of the joint portion of said holder;

FIG. 4 is a cross-sectional view taken substantially along the line II—II and as seen in the arrow direction of FIG. 3;

PREFERRED EMBODIMENT OF THE INVENTION

Figure 5:
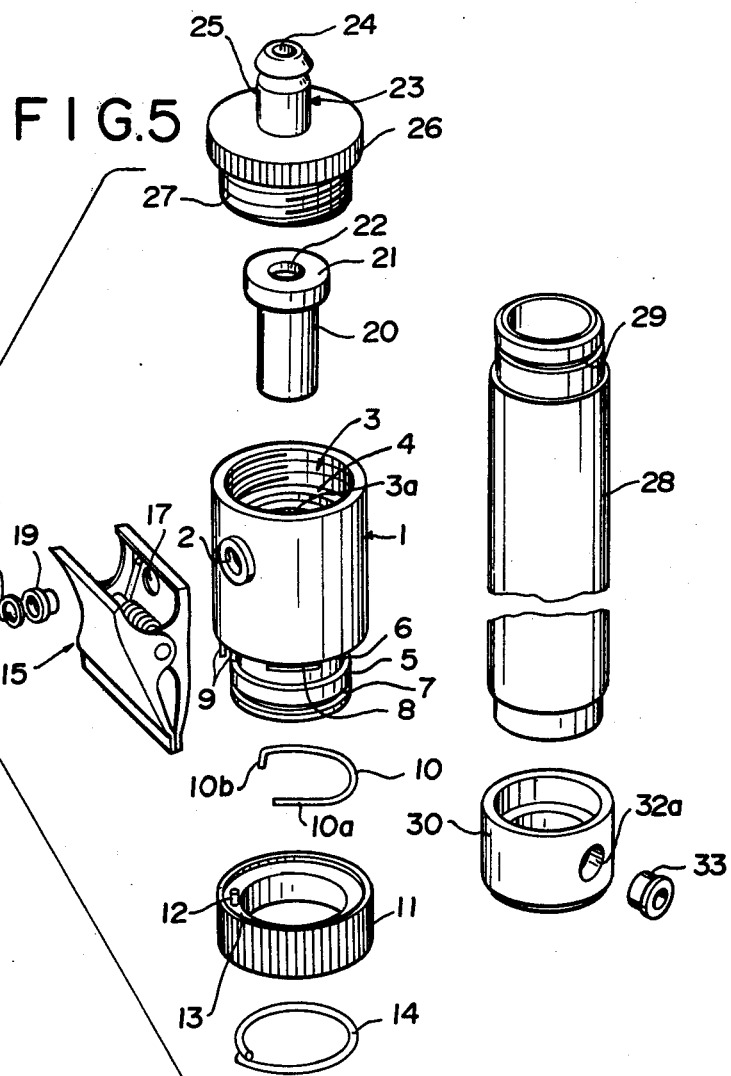
FIG. 5 is an exploded perspective view on an enlarged scale of said holder as shown in FIG. 1.

The present invention will be now described referring to the accompanying drawings which show one preferred embodiment of holder constructed in accordance with the present invention as being employed on a gas detection tube.

The gas detection tube holder of the invention substantially comprises a hollow cylindrical main body 1 formed of a suitable metal, for example and having a threaded bore 2 in the periphery thereof for the purpose to be described hereinafter. The hollow interior of the main body 1 is divided into a female threaded large diameter portion 3 and a smaller diameter plain portion (not shown) by an annular shoulder 4 which is positioned substantially in the center portion of the length of the main body. A reduced diameter hollow cylindrical extension 5 is provided at the end of the main body 1 adjacent to the smaller diameter plain portion of the main body interior and is provided with spaced and parallel inner and outer annular recesses 6 and 7 for the purpose to be described hereafter. A sector slit 8 is formed in the inner annular recess 6 and spaced angular movement regulation pins 9,9 extend outwardly from the above-mentioned end of the main body 1 for the purpose to be described hereinafter. A substantially horse shoe-shaped spring 10 formed of steel wire is received in the inner recess 6 and the spring has one straight end portion 10a and the other curved end portion formed with an inward bent 10b at the extreme end thereof. The center area of the spring straight end portion 10a protrudes through the sector slit 8 in the annular inner recess 6 into the interior of the main body 1.

An externally knurled operation ring 11 having a stepped interior including a larger diameter portion and a smaller diameter portion divided by a shoulder is received on the cylindrical extension 5 of the main body 1 for rotation with respect to the main body within a limited angular distance defined by the spaced angular movement regulation pins 9,9 on the cylindrical extension 5 of the main body 1. A pin 12 extends outwardly from the shoulder on the interior of the operation ring 11 into the larger diameter interior portion of the ring in a position between the angular movement regulation pins 9,9 to abut against either one of the pins 9,9 when the operation ring 11 is rotated relatively to the main body so as to limit the angular movement or rotation of the knurled operation ring 11 about the main body 1 and a notch 13 is formed in the inner periphery of the smaller diameter portion of the knurled operation ring 11 interior to receive the bent 10b of the spring 10 so that when the knurled ring 11 is manually rotated in one predetermined direction to resiliently deform the spring 10, the straight end portion 10a of the spring is caused to come out of the main body interior and the slit 8. A split ring 14 is disposed between the outer annular recess 7 in the main body extension 5 and the smaller diameter portion of the knurled ring interior to resiliently hold the knurled ring 11 on the main body extension 5 against inadvertent separation of the knurled ring from the extension 5.

A hinge-type clip 15 having a pair of legs is rotatably attached to the main body 1 by means of a screw 16 screwed in the threaded bore 2. One of the legs of the clip 15 has a through hole 17 the diameter of which is larger than that of the shank of the screw and a washer 18 having an opening of diameter larger than that of the shank of the screw 16 and smaller than that of the head of the screw is disposed about the screw shank on the inner side of the clip leg having the through hole and surrounds the through hole and a flanged sleeve 19 having the inner diameter substantially the same as that of the washer 18 is disposed about the screw shank with the flange disposed on the inner side of the associated clip leg. Thus, the hinge-type clip 15 can be rotated with respect to the main body 1 without loosening the screw 16. The flange 21 of the detection tube mounting member 20 serves as an air-tight packing between the detection tube mounting member 20 and the suction pipe connection member 23.

A flanged tubular detection tube mounting member 20 formed of rubber and having a flange 21 at one end is received in the smaller diameter plain portion of the interior of the main body 1 with the flange 21 seating on the shoulder on the main body interior. The tubular detection tube mounting member 20 has an axial through bore 22 extending through the flange 21 and the body of the mounting member.

A suction pipe connection member 23 having an axial through bore 24 is screwed in the holder main body 1 and integrally includes a tubular portion 25, a knurled disc portion 26 formed at one end of the tubular portion and having the outer diameter greater than that of the tubular portion and an externally male-threaded portion 27 formed on the side of the knurled disc portion 26 opposite from the tubular portion and having the outer diameter larger than that of the tubular portion and smaller than that of the knurled disc portion. The suction pipe connection member 23 is connected to the main body 1 by screwing the treated portion 27 into the female-threaded portion of the interior of the holder main body 1. When the suction pipe connection member is connected to the holder main body, the axial bore 24 aligns with the axial bore 22 in the detection tube mounting member 20 and the smaller diameter portion 3a of the holder main body 1. The tubular portion 25 of the suction pipe connection member 23 is adapted to connect at the outer end to the suction pipe (not shown) of a small-type pump (not shown) worn by a worker who will work in area where toxic gases tend to generate.

A tubular protection member 28 formed of transparent synthetic resin is detachably received at one end in the extension 5 of the holder main body 1 and extends through the smaller diameter portion of the interior of the knurled operation ring 11 and has an annular recess 29 at the reduced diameter end received in the holder main body extension 5 with the other end thereof extending out of the knurled operation ring 11. The straight end portion 10a of the spring 10 engages in the annular recess 29 at the one end of the protection member 28 to prevent the protection member from inadvertently disconnecting from the holder main body 1.

A cup-shaped end member 30 formed of metal is fitted at the extended other end of the protection member 28 and has an air passage 32 in the bottom and a bore 32a in the side for receiving a detection tube breaking means 33 for the purpose to be described hereinafter.

Figure 6:
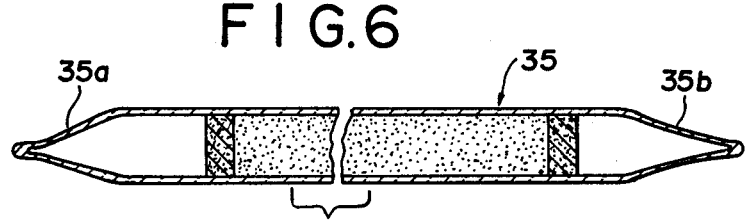
FIG. 6 is a longitudinally sectional view of one example of portable gas detection tube on which the present invention is utilized.

One example of gas detection tubes on which the holder of the present invention is shown in FIG. 6 and the illustrated gas detection tube is generally shown by reference numeral 35 and comprises an elongated transparent glass tube having the opposite tapered ends 35a and 35b. The detection glass tube has a length on the order of 10 to 20 cm and contains a reagent which changes its color when the reagent absorbs gases in a predetermined amount. The opposite ends 35a of the gas detection tube are normally welded to seal the reagent in the tube. In use, the opposite ends 35a, 35b of the glass detection tube 35 are broken by alternately inserting the tube ends into the breaking means 33 and then tilting the tube in the means 33 to an angle to allow air to pass from one end to the other end through the full length of the tube and then pressed at one end into the axial bore 22 in detection tube mounting member 20 through the axial bore 24 in the suction pipe connection member 23. After the opposite ends 35a, 35b have been broken in the manner mentioned hereinabove, the detection tube 35 is inserted into the protection member 28 via the bore 32 in the end member 30 until the leading end 35a extending beyond the adjacent end of the member 28 by a distance and the protection member 28 is then inserted into the main body extension 5 until the extending end 35a of the tube 35 is received into the mounting member 20. In order to facilitate the insertion of the gas detection tube 35 into the mounting member 20, the bore in the mounting member flares towards the end opposite from the flange 21.

After the gas detection tube 35 has been received in the holder of the invention as mentioned hereinabove, the suction pipe (not shown) extending from the small-type metering suction pump worn on an operator (not shown) by a belt (not shown) is fitted on the tubular portion 25 of the suction pump connection member 4 which is in communication with the axial bore 24 in the connection member and the clip 3 on the holder main body 1 is anchored to a portion of the operator's clothing such as a pocket on the operator's jacket, for example. Thereafter, the operator perform gas detection operation carrying the gas detection tube having the holder thereon with him.

With the above-mentioned construction and arrangement of the parts of the gas detection tube holder of the invention, in operation, the holder main body 1 having the gas detection tube connected thereto is attached to the operator's clothing by means of the clip 15 and the gas detection tube is received in the transparent protection member in the manner mentioned hereinabove and accordingly, a more precise gas detection can be obtained than when the same gas detection tube is directly worn as conventionally followed. The gas detection tube can be more conveniently worn by the operator by means of the tube holder according to the present invention and the discoloration graduation on the gas detection tube is easily visible. And the possibility of damage of the gas detection tube in the gas detection operation is reduced and the replace and wearing of the gas detection tube are quite easy.

In assembling the portable gas detection tube holder of the invention as mentioned hereinabove, the washer 18 and flanged sleeve 19 are mounted on the screw 16 and the screw 16 is screwed through the hole 17 in the clip leg into the threaded bore 2 in the main body 1 with the washer and the flange of the sleeve positioned on the inner side of the holed leg to thereby rotatably connect the clip 15 to the main body. The tubular detection tube mounting member 20 is inserted into the interior of the main body 1 until the flange 21 of the member abuts against the shoulder 4 on the main body 1 and the suction pipe connection member 23 is then screwed into the larger diameter threaded portion 3 of the main body interior. The spring 10 is snapped into the annular recess 6 in the main body extension 5 so as to protrude the center area of the straight end portion 10a through the slit 8 into the interior of the extension 5 and the split ring 14 is then snapped into the annular recess 7 in the main body extension 5 being followed by the placement of the knurled operation ring 11 about the main body extension 5. The knurled operation ring 11 is rotated until the bent 10b of the spring 10 engages in the notch 13 in the ring 11. Finally, the gas detection tube protection member 28 is inserted into the main body extension 5 until the straight end portion 10a of the spring 10 snaps into the annular recess 29 in the member 28. It is to be understood that the above-mentioned assembling order is only one example and the parts can be assembled in any other order. When the gas detection tube 35 is desired to be replaced by a new gas detection tube, the knurled operation ring 11 is rotated in the direction so as to retract the straight end portion 10a of the spring 10 out of the slit 8 and the interior of the main body extension 5 and the protection member 28 is pulled out of the knurled operation ring 11 while maintaining the spring end portion 10a in the position outside of the slit 8 and the main body extension interior.

Another example of gas detection tube device on which the present invention can be utilized is one which comprises a pair of axially aligned transparent gas detection tubes each having the reduced diameter sealed opposite ends and containing different gas detection reagents, said opposite ends adapted to be broken when a particular gas detection operation is performed, a tubular metal connection member surrounding the adjacent inner reduced diameter ends of the gas detection tube and a flexible air-tight transparent sheath.

While only one embodiment of the invention has been shown and described in detail, it will be understood that the same is for illustration purpose only and not to be taken as a definition of the invention, reference being had for the purpose to the appended claims.

What is claimed is:

1. A portable gas detection tube holder comprising a hollow cylindrical main body having two open ends, a hollow suction pipe connection member connected at one end to one end of said main body and adapted to be connected at the other end to the suction pipe of a metering pump, a clip rotatably attached to said main body for detachably securing the main body to a portion of a worker's clothing, a flanged tubular gas detection tube mounting member received in said main body between the main body and suction pipe connection member and extending towards the other end of the main body in communication with the main body and suction pipe connection member, an attachment means provided at said other end of the main body and a tubular transparent gas detection tube protection member detachably connected at one end to said attachment means and having air intake means at the other end, said protection member adapted to receive a gas detection tube extending in the axial direction of said protection member into said tubular mounting member.

2. The portable gas detection tube holder as set forth in claim 1, in which said hollow suction pipe connection member integrally includes a tubular portion for connection with said suction pipe at one end, a knurled annular disc portion connected on one side thereof to said tubular portion, a threaded portion connected at one end to the other side of said knurled annular disc portion and an axial opening extending through said tubular, disc and threaded portions; said main body has a stepped axial opening including a larger diameter threaded portion in threaded engagement with said threaded portion of the suction pipe connection member and a reduced diameter plain portion and a reduced diameter hollow extension at the other end of the main body which forms a part of said attachment means and said detection tube mounting member is formed of rubber and includes a flange seating on the shoulder defined between said threaded larger diameter portion and smaller diameter plain portion and a tubular portion received in said extension of the main body.

3. The portable gas detection tube holder as set forth in claim 1, in which said attachment means for said protection member comprises a reduced diameter extension extending from the other end of the main body and having a first annular recess provided with a slit and a second annular recess spaced from said first recess, a knurled operation ring mounted on said extension of the main body such that said knurled operation ring's rotation is limited about the extension and prevented from coming off the extension and an annular protection member anchoring spring in the form of a steel wire wound about the extension and having one straight end portion partially protruding through said slit of the first annular recess into the interior of the main body extension and the other end provided at the extreme end thereof with a bent engaging said knurled operation ring.

4. A gas detection tube holder comprising a hollow cylindrical main body having an axial stepped through opening including a larger diameter threaded portion and a smaller diameter plain portion connected together by a shoulder, said main body including a side wall having a threaded bore therein; a flanged tubular detection tube mounting member including a tubular body received in said smaller diameter plain portion and a flange sitting on said shoulder; a hollow suction pipe connection member having an axial through bore and integrally including a tubular portion adapted to be connected to the suction pipe of a metering pump worn by a worker, a knurled disc portion connected on one side to one end of said tubular portion and threaded portion connected to the other side of said disc portion and screwed in said larger diameter threaded portion of the opening of the main body; a hinge-type clip rotatably connected to said main body by means of fastening means screwed in said thread bore in the main body; a knurled operation ring, a means for connecting said knurled operation ring to said main body such that said knurled operation ring has limited rotational movement relative to the main body; and a transparent tubular gas detection tube protection member detachably connected at one end to said knurled operation ring and having at its other end an end member provided with a gas detection tube breaking means and air intake means.

5. The gas detection tube holder as set forth in claim 4, in which said connecting means comprises a hollow reduced diameter extension provided at the end of said main body adjacent to said smaller diameter plain opening portion of the main body and having first and second annular recesses in the outer periphery, said first annular recess including a sector slit, a spring in the form of steel wire having one straight end portion bridging said slit with a center section thereof protruding into the interior of said extension and a bent formed at the extreme end of the other end portion of said spring, a notch formed in the interior of said knurled operation ring for receiving said bent of the spring, a split ring snapped in said second annular recess of the extension in abutment against said knurled operation ring and said tubular gas detection tube protection member having an annular recess formed at one end of said protection member for receiving said straight end portion of the spring.

6. The gas detection tube holder as set forth in claim 4, in which the rotational movement of said knurled operation ring relative to said main body is limited by means of two spaced pins extending from the end of said main body adjacent to said extension and a pin extending from said knurled operation ring to a position between said spaced pins on the main body to selectively engage the latter pins.

7. The gas detection tube holder as set forth in claim 4, in which said fastening means includes a screw passing through one leg of said hinge-type clip and screwed in said threaded bore in the main body, and a washer and a flanged sleeve mounted on said screw.

8. The gas detection tube holder as set forth in claim 4, in which said gas detection tube protection member is formed of a transparent synthetic resin and receives a gas detection tube with one end of said detection tube extending beyond the adjacent end of the protection member into said gas detection tube mounting member.

9. The gas detection tube holder as set forth in claim 8, in which said gas detection tube mounting member is formed of rubber and having an outwardly flaring opening for receiving said extending end of the gas detection tube.

* * * * *